Oct. 24, 1939. J. C. RASMUSSEN Plant Pat. 344
CARNATION
Filed May 5, 1939
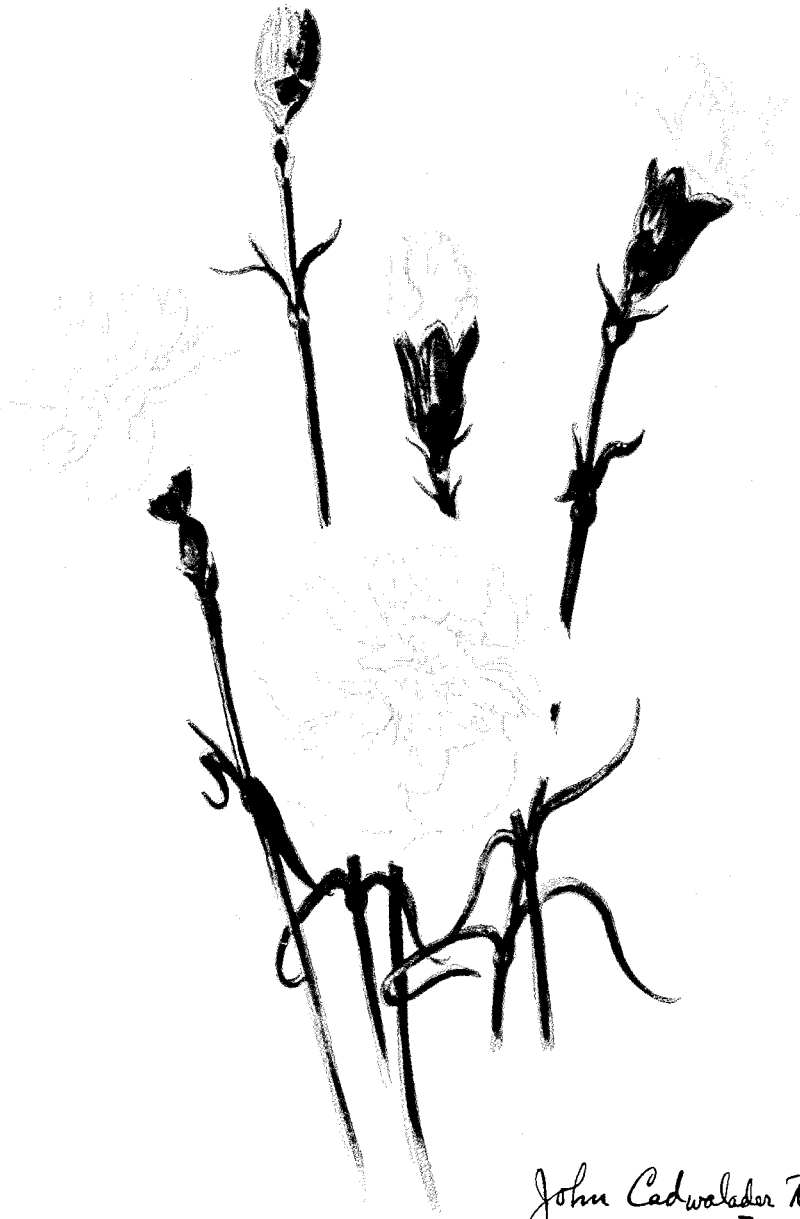
John Cadwalader Rasmussen
INVENTOR
By Orville M. Kile
PLANT PATENT AGENT Patented Oct. 24, 1939

Plant Pat. 344

UNITED STATES PATENT OFFICE

344

CARNATION

John Cadwalader Rasmussen, New Albany, Ind.

Application May 5, 1939, Serial No. 271,995

1 Claim. (Cl. 47—60)

The object of my invention is to produce a superior light pink forcing carnation and particularly to improve upon the variety Laddie. This new variety is the result of definite breeding efforts and is a cross between two unnamed and undisseminated seedlings both of which had Laddie as one of the parents. The new variety has been asexually reproduced and its novel characteristics appear to be firmly fixed.

The original illustrations accompanying this application show three flowers and two buds of this variety, with portions of the stems and leaves, in approximately their true colors and slightly reduced in size, also a single petal.

Following is a detailed description of this new variety. Color references indicate Ridgway's Color Standards and Nomenclature and where there are no plate references the ordinary dictionary term is intended.

*The plant*

Growth:

Very vigorous; health; branches freely and produces a very bushy plant.

Productivity:

Produces a large number of flowers and its cuttings root almost one hundred percent. It produces seed as a female parent.

Foliage:

Moderate in quantity; general appearance blue-green.

*Leaves.*—¼ to ⅜ in. wide. Dusky Green (Plate XXXIII) covered with light gray bloom.

Stems:

Very strong and long; same color as leaves; first internode usually very short, permitting the first set of leaves to embrace the calyx.

*The flower*

Bud:

*Size.*—Medium.

*Shape.*—Slender and moderately long.

*Calyx.*—Very tough and non-splitting. In no case has a split calyx ever been found in this variety. This is an excellent quality in a large carnation.

Blossom:

*Form.*—Symmetrical; high centered. Some of the central petals are very much shorter than others, allowing considerable space between the longer ones and thus producing an open and irregular effect.

*Size.*—Three to three and one-half inches in diameter.

*Petalage.*—Usually about 50 petals, including 8 or 10 petaloids which are formed at the end of some of the filaments and take the place of many of the anthers.

*Petals.*—Size—one and one-half inches wide by two and one-fourth inches long, approximately one inch of the length being the shank. Shape—usual wedge shape; edges only slightly serrated. Texture—substantial. Color—rather evenly distributed over the visible portions of the petals and lies between Hermosa Pink (Plate I) and Alizarine Pink (Plate XIII) with a touch of Jasper Pink (Plate XIII) in the shaded portions. This color holds well, fading to no marked degree during bright weather.

*Longevity.*—As a cut flower the keeping qualities are excellent.

*Fragrance.*—Moderate cinnamon fragrance.

*Reproductive organs*

Stamens:

Few; irregular lengths; several topped with petaloids rather than with anthers.

*Filaments.*—Slender; white.

*Anthers.*—Cream Color (Plate XVI); few, mostly replaced by petaloids.

Pistils:

Two, arising from top of ovary; white; one and one-fourth inches in length; slightly curved at tip.

Ovary:

Medium size; deeply lobed; contains many ovules.

*Comparison*

Laddie is the known variety of carnation which is most like my new variety and over which my invention is an improvement. My new variety is similar to Laddie in its height of growth and color of foliage but differs from Laddie principally in the following points:

1. Its productivity is much greater than that of Laddie.
2. It produces seed as the female parent while Laddie seldom does.
3. Its cuttings root almost one hundred percent whereas Laddie is very difficult to root.
4. It branches more freely when topped and produces a bushier plant than does Laddie.
5. Its leaves are slightly narrower than those of Laddie.
6. Grown under the same conditions its blossoms are slightly smaller than those of Laddie.

7. The form of its blossoms is more perfect and symmetrical than that of Laddie's blossoms.

8. Its blossoms are of a slightly darker shade than those of Laddie and do not fade.

Having thus disclosed my invention, I claim:

The new and distinct variety of carnation substantially as herein shown and described, characterized particularly by its habit of rooting readily; its healthy, free-branching and bushy growth; its long, strong stems; its non-splitting calyx; and its symmetrical flower of Hermosa Pink to Alizarine Pink which fade but little during bright weather.

JOHN CADWALADER RASMUSSEN.